United States Patent
Chatterjee et al.

(10) Patent No.: US 10,456,071 B2
(45) Date of Patent: Oct. 29, 2019

(54) SYSTEM AND METHOD FOR ESTIMATING COGNITIVE TRAITS

(71) Applicant: Tata Consultancy Services Limited, Mumbai (IN)

(72) Inventors: Debatri Chatterjee, Kolkata (IN); Aniruddha Sinha, Kolkata (IN); Rajat Kumar Das, Kolkata (IN); Shreyasi Datta, Kolkata (IN)

(73) Assignee: Tata Consultancy Services Limited, Mumbai (IN)

( * ) Notice: Subject to any disclaimer, the term of this patent is extended or adjusted under 35 U.S.C. 154(b) by 99 days.

(21) Appl. No.: 15/523,241

(22) PCT Filed: Apr. 7, 2016

(86) PCT No.: PCT/IB2016/051972
§ 371 (c)(1),
(2) Date: Apr. 28, 2017

(87) PCT Pub. No.: WO2016/162820
PCT Pub. Date: Oct. 13, 2016

(65) Prior Publication Data
US 2018/0014768 A1 Jan. 18, 2018

(30) Foreign Application Priority Data
Apr. 7, 2015 (IN) .................. 1444/MUM/2015

(51) Int. Cl.
*A61B 5/16* (2006.01)
*G06K 9/62* (2006.01)
(Continued)

(52) U.S. Cl.
CPC ............ *A61B 5/16* (2013.01); *A61B 5/04014* (2013.01); *A61B 5/04017* (2013.01);
(Continued)

(58) Field of Classification Search
CPC ........... A61B 5/16; A61B 5/162; A61B 5/165; A61B 5/167; A61B 5/168
See application file for complete search history.

(56) References Cited

U.S. PATENT DOCUMENTS

| 2008/0058668 A1 | 3/2008 | Seyed Momen et al. |
| 2008/0080786 A1 | 4/2008 | Mitchell et al. |

(Continued)

OTHER PUBLICATIONS

Wang et al., "Automatic Removal of Ocular Artifacts from Electroencephalogram using Hilbert-Huang Transform," 2nd International Conference on Bioinformatics and Biomedical Engineers 2008, p. 2138-2141. (Year: 2008).*

(Continued)

*Primary Examiner* — Thaddeus B Cox
(74) *Attorney, Agent, or Firm* — Finnegan, Henderson, Farabow, Garrett & Dunner LLP (57) ABSTRACT

The present disclosure envisages a computer implemented system and method to derive a relationship between Elementary Cognitive Tasks (ECTs) and the underlying cognitive skills of individuals through Electroencephalogram (EEG) analysis. The aim is to evaluate or improve the perceptual-cognitive traits of a subject that comprises disintegrating a given task into elementary task that are further mapped to identified cognitive categories of Bloom's Taxonomy, upon which a cluster analysis is performed. The separation index between the clusters thereafter establishes that individuals have different thinking process which is characteristics of that subject.

18 Claims, 4 Drawing Sheets

(51) Int. Cl.
　　　*A61B 5/00*　　　(2006.01)
　　　*A61B 5/0484*　(2006.01)
　　　*A61B 5/04*　　　(2006.01)
　　　*G16H 20/70*　　(2018.01)
　　　*G16H 50/30*　　(2018.01)
　　　*G16H 50/20*　　(2018.01)
　　　*G09B 19/00*　　(2006.01)

(52) U.S. Cl.
　　　CPC ...... *A61B 5/04842* (2013.01); *A61B 5/04845* (2013.01); *A61B 5/167* (2013.01); *A61B 5/7203* (2013.01); *A61B 5/7253* (2013.01); *A61B 5/7264* (2013.01); *G06K 9/6231* (2013.01); *G16H 20/70* (2018.01); *G16H 50/20* (2018.01); *G16H 50/30* (2018.01); *A61B 5/162* (2013.01); *G09B 19/00* (2013.01)

(56) References Cited

U.S. PATENT DOCUMENTS

| | | |
|---|---|---|
| 2014/0220540 A1 | 8/2014 | Burgin et al. |
| 2014/0316230 A1 | 10/2014 | Denison et al. |
| 2014/0330159 A1 | 11/2014 | Costa et al. |

OTHER PUBLICATIONS

International Search Report from the U.S. Patent Office in International Application No. PCT/IB2016/051972 dated Aug. 22, 2016.

\* cited by examiner

SYSTEM AND METHOD FOR ESTIMATING COGNITIVE TRAITS

CROSS REFERENCE TO RELATED APPLICATIONS

This application is a U.S. National Stage Filing under 35 U.S.C. § 371 and claims priority from International Application No. PCT/IB2016/051972, filed on Apr. 7, 2016, which application claims priority under 35 U.S.C. § 119 from India Application No. 1444/MUM/2015, filed on Apr. 7, 2015. The entire contents of the aforementioned applications are incorporated herein by reference.

TECHNICAL FIELD

This disclosure relates generally to the field of perceptual cognitive traits, and more particularly to a system and method of estimating and improvising perceptual-cognitive traits of a subject.

BACKGROUND

Cognitive load, in general, is defined by the amount of short term memory used by an individual for a given task and primarily depends on how an individual perceives, assimilates and responds to an external stimulus. Usually, the actions of an individual are mediated and influenced by external environment and ability of an individual to understand and effectively interact with the environment is dependent on the cognitive traits of an individual. Hence in order to achieve the best results and exhibit best performance, the cognitive load on the individual should be optimum since too much cognitive load might result in stress, anxiety, etc. On the other hand, very less cognitive load is actually a un-utilization of one's cognitive capacity and ability.

It will however be agreeable that optimum level of cognitive load may vary from one individual to another, and is basically dependent on inherent cognitive skills of an individual. Developing basic cognitive skills of an individual, however remains an ardent task, to which education has a supreme role to play. The process by which a person learns best is also different across different people.

Bloom's taxonomy of learning domains is known to promote higher forms of thinking in education such as analyzing and evaluating concepts, processes, procedures, and principles. It majorly defines six major categories of cognitive skills that are arranged according to the increasing order of cognitive maturity as knowledge, comprehension, application, analysis, synthesis and evaluation. There are usually two measures of cognitive load:

a) Subjective Measures of Cognitive Load—This domain has been well read by many to find that various instructional methods can be used to improve the short term memory operations b) Objective Measures of Cognitive Load—This includes estimation using different physiological signals and in order to measure the cognitive skills of an individual, particularly in the field of education area is relatively a new area of search. To make it more accessible, the sensing mechanism needs to be low cost and commercially available.

Recently, there have been various works to analyze the cognitive load of an individual for a given task using commercial EEG devices. As part of the education psychology, the cognitive load is analyzed based on the continuous EEG signals during the learning from hypertext and multimedia contents. EEG signals are being used in diverse application areas like estimation of video quality, ease of reading texts, and scientific problem solving. Apart from EEG, other physiological parameters like eye tracking, skin conductance and heart-rate are also used to investigate the effect of stimulus on the mental stress. There has been an attempt in past to study the students' learning trajectories and teachers' effect on problem solving abilities, however there has been complete reliance on the students' outcomes and never used brain signals. Many have also used Elementary Cognitive Tasks (ECTs) to investigate how the level of complexity (low and high cognitive load) manifests in the EEG and various physiological parameters.

However, none of the above works objectively analyze the relationships between the various ECTs or focus on investigating the relationship between the ECTs and Bloom's categories.

OBJECTIVES

In accordance with the present invention, the primary objective is to provide a system and method for analyzing elementary cognitive tasks with Bloom's Taxonomy using low cost commercial EEG device.

Another objective of the invention is to provide a system and method to objectively analyze the relationship among various ECTs and also between various elementary cognitive tasks (ECTs) and Bloom's categories.

Another objective of the invention is to provide a system and method to characterize an unknown stimulus and also derive various performance attributes of a subject.

Yet another objective of the invention is to provide a method and system for estimating or improvising perceptual-cognitive traits of a subject by creating Electroencephalogram (EEG) models for the cognitive skills defined in the Bloom's taxonomy.

A further object of this disclosure is to evaluate cognitive behavior of an individual using duster analysis of EEG features for different stimuli or tasks.

Other objects and advantages of the present invention will be more apparent from the following non-restrictive description of illustrative embodiments thereof, when read in conjunction with the accompanying figures, which are not intended to limit the scope of the present disclosure.

SUMMARY

Before the present methods, systems, and hardware enablement are described, it is to be understood that this invention in not limited to the particular systems, and methodologies described, as there can be multiple possible embodiments of the present invention which are not expressly illustrated in the present disclosure. It is also to be understood that the terminology used in the description is for the purpose of describing the particular versions or embodiments only, and is not intended to limit the scope of the present invention which will be limited only by the appended claims.

Accordingly, in a preferred embodiment the disclosure provides a method for estimating or improvising perceptual-cognitive traits of a subject. The steps for estimating perceptual-cognitive traits of a subject comprise, firstly retrieving and pre-processing the data and associated metadata indicative of brainwave activity of the subject to obtain effect of a plurality of elementary cognitive tasks, followed by identification of cognitive categories within a cognitive domain of cognitive learning model. Next, plurality of elementary cognitive tasks to be performed by the subject are mapped with the identified cognitive categories and duster analysis on each of the mapped elementary cognitive tasks is performed. Further, separation index values are determined from cluster analysis in relation to the identified cognitive categories and finally metrics are generated from the separation index values to estimate the perceptual-cognitive traits of a subject.

According to another embodiment of the disclosure, the data is electroencephalogram (EEG) signals captured using low resolution EEG devices.

In one significant embodiment of the present disclosure, the system for estimating and improvising perceptual-cognitive traits of a subject is disclosed. The system broadly comprises a processor, a data bus coupled to said processor; and a computer-usable medium embodying computer code, said computer-usable medium being coupled to said data bus, said computer program code comprising instructions executable by said processor and configured for:

retrieving and pre-processing data and associated metadata indicative of brainwave activity of the subject to obtain a plurality of elementary cognitive tasks;

identifying cognitive categories within a cognitive domain of cognitive learning model;

mapping plurality of elementary cognitive tasks to be performed by the subject with identified cognitive categories;

performing duster analysis on each of the mapped elementary cognitive tasks and determining separation index values therefrom the cluster analysis in relation to the identified cognitive categories; and generating metrics from the separation index values for estimation or improvisation of perceptual-cognitive traits of the subject.

BRIEF DESCRIPTION OF THE DRAWINGS

The foregoing summary, as well as the following detailed description of preferred embodiments, are better understood when read in conjunction with the appended drawings. For the purpose of illustrating the invention, there is shown in the drawings exemplary constructions of the invention; however, the invention is not limited to the specific methods and system disclosed. In the drawings.

DETAILED DESCRIPTION

Some embodiments of this invention, illustrating all its features, will now be discussed in detail.

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

It must also be noted that as used herein and in the appended claims, the singular forms "a," "an," and "the" include plural references unless the context clearly dictates otherwise. Although any systems and methods similar or equivalent to those described herein can be used in the practice or testing of embodiments of the present invention, the preferred, systems and methods are now described.

The disclosed embodiments are merely exemplary of the invention, which may be embodied in various forms.

The elements illustrated in the Figures interoperate as explained in more detail below. Before setting forth the detailed explanation, however, it is noted that all of the discussion below, regardless of the particular implementation being described, is exemplary in nature, rather than limiting. For example, although selected aspects, features, or components of the implementations are depicted as being stored in memories, all or part of the systems and methods consistent with the attrition warning system and method may be stored on, distributed across, or read from other machine-readable media.

The techniques described above may be implemented in one or more computer programs executing on (or executable by) a programmable computer including any combination of any number of the following: a processor, a storage medium readable and/or writable by the processor (including, for example, volatile and non-volatile memory and/or storage elements), plurality of input units, and plurality of output devices. Program code may be applied to input entered using any of the plurality of input unit to perform the functions described and to generate an output displayed upon any of the plurality of output device.

Each computer program within the scope of the claims below may be implemented in any programming language, such as assembly language, machine language, a high-level procedural programming language, or an object-oriented programming language. The programming language may, for example, be a compiled or interpreted programming language. Each such computer program may be implemented in a computer program product tangibly embodied in a machine-readable storage device for execution by a computer processor.

Method steps of the invention may be performed by one or more computer processors executing a program tangibly embodied on a computer-readable medium to perform functions of the invention by operating on input and generating output. Suitable processors include, by way of example, both general and special purpose microprocessors. Generally, the processor receives (reads) instructions and data from a memory (such as a read-only memory and/or a random access memory) and writes (stores) instructions and data to the memory. Storage devices suitable for tangibly embodying computer program instructions and data include, for example, all forms of non-volatile memory, such as semiconductor memory devices, including EPROM, EEPROM, and flash memory devices; magnetic disks such as internal hard disks and removable disks; magneto-optical disks; and CD-ROMs. Any of the foregoing may be supplemented by, or incorporated in, specially-designed ASICs (application-specific integrated circuits) or FPGAs (Field-Programmable Gate Arrays). A computer can generally also receive (read) programs and data from, and write (store) programs and data to, a non-transitory computer-readable storage medium such as an internal disk (not shown) or a removable disk.

Any data disclosed herein may be implemented, for example, in one or more data structures tangibly stored on a non-transitory computer-readable medium. Embodiments of the invention may store such data in such data structure(s) and read such data from such data structure(s).

Definitions

Bloom's Taxonomy: Bloom's Taxonomy is an essential model for promoting higher forms of thinking in an individual by providing appropriate learning conditions. Bloom's taxonomy classifies different learning objectives into three domains, namely, Cognitive, Affective and Psychomotor, and the element of discussion for present disclosure is Cognitive domain that involves knowledge, comprehension, application, analysis and evaluation of a particular topic.

Cognitive load primarily depends on how an individual perceives, assimilates and responds to an external stimulus. The present disclosure attempts to create Electroencephalogram (EEG) models for the cognitive skills defined in the Bloom's taxonomy using low cost, commercial EEG devices.

The present disclosure comprises a system which may be used for estimating and improvising perceptual-cognitive traits of a subject. The embodiments of the present disclosure may be applied in educational psychology to provide individual assistance according to one's learning style and traits, although it should be understood that the scope of the present invention is in no way limited to these applications.

Figure 1:
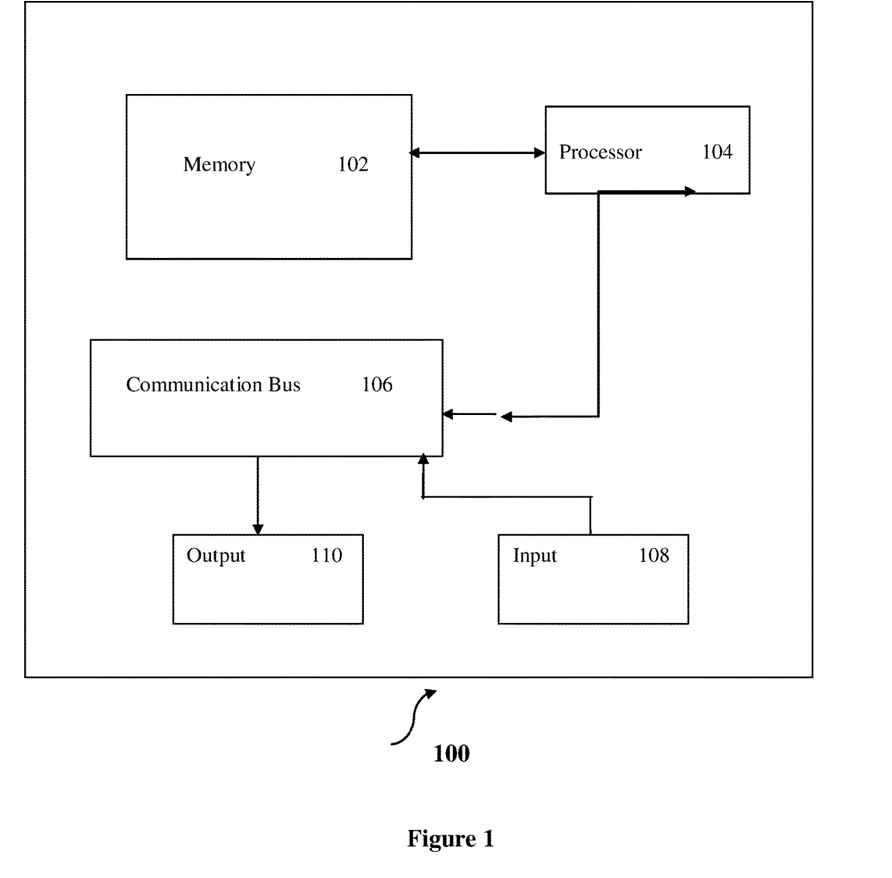
FIG. 1 of the present disclosure is a schematic functional block diagram of an exemplary architecture for the system, in accordance with one embodiment of present disclosure.

In an embodiment of the present disclosure, as presented in FIG. 1, the system 100 comprises a processor 104, a data bus 106 coupled to said processor 104, and a computer-usable medium like a memory 102 embodying computer code and coupled to a data bus 106, wherein the computer program code comprises instructions executable by said processor 104 and is configured to relate the brain signals generated by various cognitive tasks to different cognitive categories of Bloom's taxonomy. The actual modulations originating in brain are captured which in turn control the ultimate thinking process for each and every response/action, eventually enabling measurement of improvisation in cognitive skills of an individual.

While different techniques may be used for reading and analyzing brain function, most widely used ones being—Electroencephalogram (EEG), functional magnetic resonance imaging (fMRI), functional near infra-red spectroscope (fNIRs), positron emission tomography (PET) etc. For the purposes of present disclosure, EEG has been selected as it is a non-invasive and relatively in-expensive method having excellent temporal resolution. More specifically, 14 lead EEG device from Emotiv has been used for capturing and analyzing brain signals.

A set of Elementary Cognitive Tasks (hereinafter referred to as ECTs) focusing on visual perceptions and cognitive speed is recognized and defined as the stimulus as ECTs are directly linked with general mental ability and intelligence of an individual. As a non-limiting example, the factors that are being considered for visual perception includes speed of closure and flexibility of closure.

In one exemplary embodiment, the stimulus is presented and EEG data and associated metadata is captured using python based capture tool. For EEG data collection a 14-lead Emotiv headset is used. The subject is presented with a set of questions that he is expected to answer using any of plurality of input devices 108 (referring to FIG. 1)—a cursor control, such as a mouse, a trackball, or cursor direction keys for communicating information and command selections to processor. After completion of questionnaire and data collection process, the subject is evaluated in terms of response time and accuracy and the result is displayed on the commonly known output device 110 (shown in FIG. 1).

Figure 2:
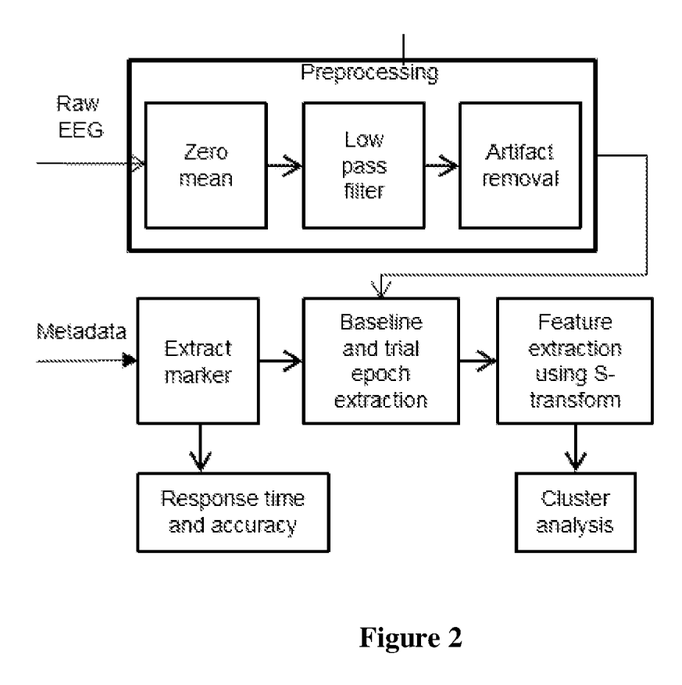
FIG. 2 is a block diagram illustrating the flow of EEG signal processing, in accordance with one embodiment of present disclosure.

The EEG signals and associated metadata are analyzed as depicted in FIG. 2. The metadata may include the time stamps for the EEG signals; presentation time of the stimulus, instruction and fixation slides; time stamps and the entries of the user responses. The relation between the accuracy and the response time of the subjects for each stimulus are analyzed.

The raw EEG signal is preprocessed and segmented based on predefined markers and then analyzed in time-frequency domain for feature extraction and clustering as shown in FIG. 2. First in the pre-processing step, the signal is normalized to zero mean and fed to a low pass filter of predefined frequency range, e.g. 35 Hz to limit the signal to the frequency band of interest. EEG signal is vulnerable to different artifacts, the dominant of them being the eye blink related artifact.

One of the described embodiments of the present disclosure, Hilbert-Huang Transform (HHT) based approach is used to remove the artifact. After that the clean data is segmented into baseline and trial epochs. Then these epochs are partitioned in windows of N seconds with 50% overlap.

In one selected embodiment, N is selected to be 20 seconds for baseline epoch and 5 seconds for trial epochs. This is particularly done to examine multiple trial windows with a single baseline window. Both the trial and baseline windows are decomposed in the time-frequency domain using S-transform of N seconds with 50% overlap. From this decomposition the mean frequencies are computed using the following formula:

$$f(\omega) = \frac{\sum_{i=0}^{n-1} I_{\omega(i)} f_{\omega(i)}}{\sum_{i=0}^{n-1} I_{\omega(i)}} \quad (1)$$

Where $\omega$ is the frequency band under analysis, n is the number of frequency bins in $\omega$, $f_i$ is the frequency at bin i and $I_i$ is the energy density of $\omega$ at frequency bin i In a single window, the maximum and average powers of all the mean frequencies are extracted for both trial and baseline. Finally the feature vector is computed with the peak and average energy shifts ($\Delta E^{Ii}_{max}$, $\Delta E^{Ii}_{avg}$), the corresponding frequency shifts ($\Delta f^{Ii}_{max}$, $\Delta f^{Ii}_{avg}$) between the baseline and trial in the frequency band i for channel I. Here both alpha ($\alpha$) and theta ($\theta$) bands are considered. The feature vectors used are given by (2), where $F^I_{peak}$ and $F^I_{mean}$ respectively denote the feature vectors comprising features computed from maximum and average powers of all the mean frequencies for channel I.

$$\left. \begin{array}{l} F^I_{peak} = \{\Delta E^{I,\alpha}_{max}, \Delta f^{I,\alpha}_{max}, \Delta E^{I,\theta}_{max}, \Delta f^{I,\theta}_{max}, L^I_{max}\} \\ F^I_{mean} = \{\Delta E^{I,\alpha}_{avg}, \Delta f^{I,\alpha}_{avg}, \Delta E^{I,\theta}_{avg}, \Delta f^{I,\theta}_{avg}, L^I_{avg}\} \end{array} \right\}, 1 \leq I \leq 14 \quad (2)$$

where $L^1_{max}$ or $L^1_{avg}$ is defined as the cognitive load, computed taking maximum or average powers respectively and $1 \leq I \leq 14$ denotes the 14 leads of the Emotiv EEG device. The final feature vectors $F_{peak}$ and $F_{mean}$ are obtained by concatenating the vectors $F^I_{peak}$ or $F^I_{mean}$ respectively for all I. Feature selection is performed to select a subset of the above EEG features. If f is the number of features per channel of EEG data then the feature vectors from all 14 channels are concatenated to form $R^{14f}$ dimensional feature vector.

The ECT or stimulus is categorized according to Bloom's categories; Table 1 below depicts mapping of stimulus or ECTs to identified Bloom's categories, namely Understand, Remember and Analyze. However, it has to be understood that the identification of three given Bloom's categories is only for exemplary purposes. Similar mapping can be done for Bloom's six categories namely remember, understand, apply, analyze, evaluate and create.

TABLE 1

Mapping Stimuli to Bloom's Categories

| Stimulus | Task Details | Measure | Relationship to Bloom's category |
|---|---|---|---|
| 1. Scattered X's (SX) | Find number of times 'X' appears on screen | Perceptual Speed | Understand & Remember |
| 2. Finding A (FA) | Count words containing 'a' from a full page of words | Perceptual Speed | Analyze & Remember |
| 3. Hidden Pattern (HP) | Find a target pattern from a list of five complex patterns | Flexibility of closure | Analyze |
| 4. Visual Pursuit (VP) | Count the number of occurances of a target image from an array of multiple complex images | Perceptual Speed | Understand & Remember |
| 5. Finding Number (FN) | Count the non-matching number pairs from a list of number pairs | Perceptual Speed | Understand & Remember |
| 6. Gestalt closure test (GC) | Look at an incomplete image and identify the object | Speed of closure | Understand |

The EEG signals are first cleaned from various artifacts and then analyzed using standard machine learning techniques. Having also identified the cognitive categories within the Bloom's taxonomy and mapped plurality of ECTs with identified cognitive domains of Bloom's taxonomy, a cluster analysis is performed on the features of EEG signals using K-means algorithm. An unsupervised approach has been adapted to objectively measure the effects of various ECTs on individual subjects.

An optimum number of clusters for an individual are identified by performing K means based clustering on the EEG features. Referring to afore-given non limiting description of illustrative embodiment wherein 6ECTs have been identified, the K is varied from 2 to 10. The value of K that generates compact clusters and also separates the clusters well, is determined using the minimum Xie-Beni index, in accordance with one exemplary embodiment of present disclosure. Further, relationships between the clusters in terms of distance between the centroids and the insights with the Bloom's categories are determined. It should however be noted that the scope of the invention is in no way limited to this example, and alternative variations of this task or given ECTs are possible and included within the scope of the invention.

Let, referring to above example, the maximum number of minimum time response is obtained in the task "Finding A" (FA) and maximum number of maximum time response is obtained in "Visual Pursuit" (VP) task. Similarly let maximum accuracy is achieved in FA and minimum accuracy is achieved for "Hidden Pattern" (HP). Thus FA provides maximum accuracy at minimum response time.

For exemplary purposes, all the tasks are of comparable load with a slight variation in their spread. As all the ECTs impart similar levels of cognitive load upon the subjects, the choice for the stimuli is justified.

Figure 3:
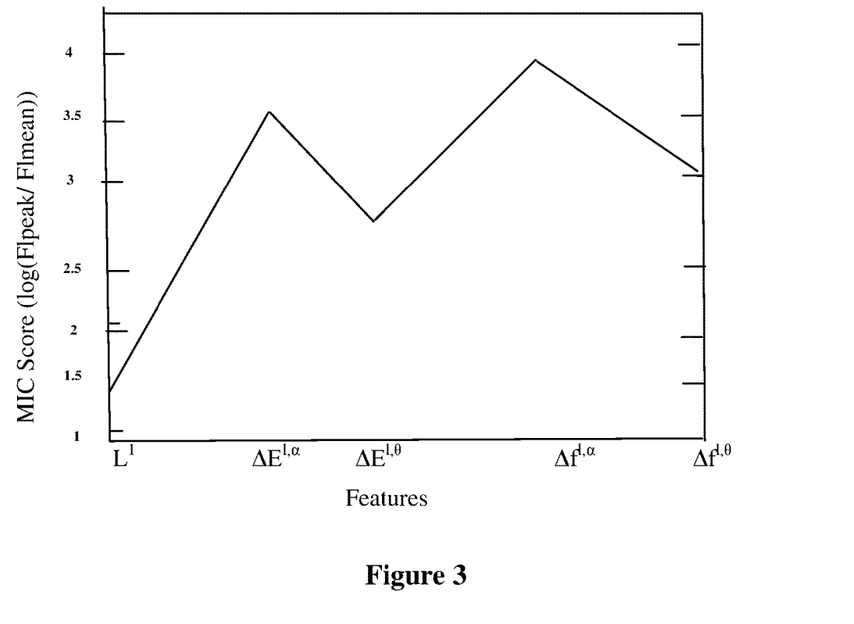
FIG. 3 is a graph showing comparison of various feature components for $F^I_{peak}$ $F^I_{mean}$ in accordance with one preferred embodiment of present disclosure.

Next, a feature selection is performed on the total feature list given in equation (2) above. Maximal Information Co-efficient (MIC) is used to choose the most appropriate feature subset among $F^I_{peak}$ and $F^I_{mean}$. The MIC score of the corresponding peak ($F^I_{peak}$) and mean ($F^I_{mean}$) feature ratios in logarithmic unit is shown in FIG. 3. The positive values indicate that $F^I_{peak}$ is a better subset. Here individual features' MIC values are averaged across all 14 channels and then summed over all the participants.

Figure 4:
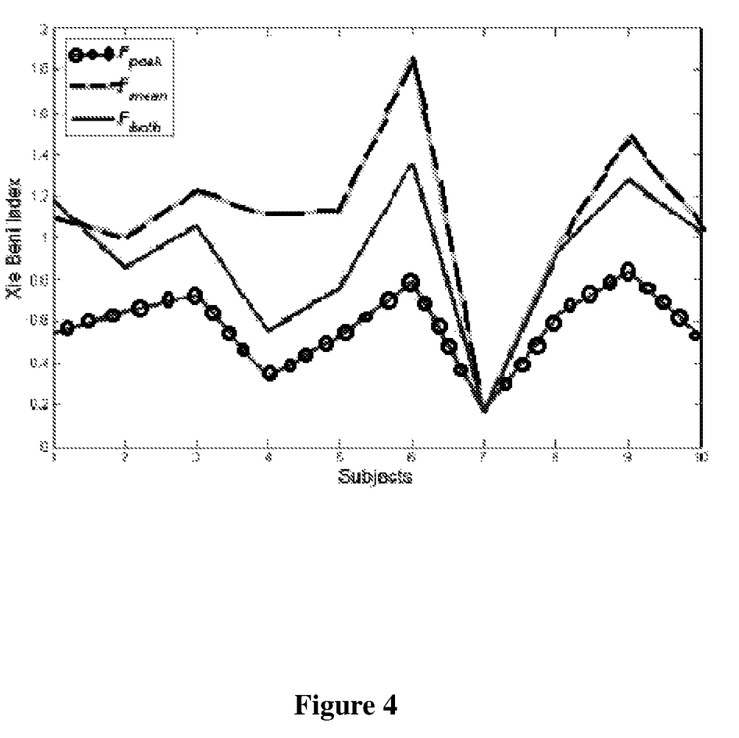
FIG. 4 is a graph showing result of Xie-Beni index variation among subjects for different feature combinations, in accordance with one embodiment of present disclosure.

While performing the cluster analysis, firstly the effects of taking peak energy and frequency shifts, average energy and frequency shifts or both in the feature vector are analyzed. This is illustrated in FIG. 4. It can be observed that taking a five dimensional feature vector $F_{peak}$ gives the best clustering performance (in terms of smaller Xie Beni Indices) compared to $F_{mean}$ or a ten dimensional feature vector $F_{both}$, where $F_{both} = \{F_{peak}, F_{mean}\}$. Hence all further analyses are carried out using only $F_{peak}$ as feature.

As can be seen from Table II below, results obtained from clustering analysis in terms of Xie-Beni indices have been summarized.

TABLE II

XIE BENI INDEX FOR DIFFERENT SUBJECTS AND FEATURES

| Subject ($K_{min}$) | Features | | | | | | |
|---|---|---|---|---|---|---|---|
| | F1 | F2 | F3 | F4 | F5 | F6 | F7 |
| S1 (6) | 1.9786 | 1.0073 | 2.2869 | 0.9156 | 1.0671 | 0.8103 | 0.8366 |
| S2 (6) | 1.7380 | 0.7125 | 0.8235 | 0.8935 | 0.7652 | 0.6745 | 0.6413 |
| S3 (6) | 1.7120 | 0.6637 | 1.1722 | 0.8462 | 1.2651 | 0.9040 | 0.7244 |
| S4 (6) | 1.3938 | 0.3777 | 1.2208 | 0.4630 | 1.2085 | 0.5866 | 0.3305 |
| S5 (6) | 1.3834 | 0.7948 | 0.9361 | 0.5566 | 1.6100 | 0.6423 | 0.5830 |
| S6 (6) | 2.3961 | 1.0465 | 0.9508 | 0.7961 | 2.4843 | 0.9268 | 0.7878 |
| S7 (2) | 0.8770 | 0.1607 | 1.2089 | 0.1583 | 0.9118 | 0.6000 | 0.1648 |
| S8 (6) | 1.0398 | 0.4943 | 1.1652 | 0.8390 | 1.0400 | 0.7440 | 0.6183 |
| S9 (6) | 1.2961 | 0.9185 | 1.5184 | 0.9483 | 0.8828 | 0.7383 | 0.8391 |
| S10 (6) | 1.7442 | 0.6232 | 1.5616 | 0.6209 | 0.8355 | 0.7891 | 0.5216 |

Here $F_1$ to $F_5$ denote the following features:
$F_1 = L^1_{max}$, $F_2 = \Delta E^{T,\alpha}_{max}$, $F_3 = \Delta f^{T,\alpha}_{max}$, $F_4 = \Delta E^{T,\theta}_{max}$, $F_5 = \Delta f^{T,\theta}_{max}$ $F_6$ is a combination of the $F_1$ through $F_5$ while $F_7$ is a combination of $F_2$ and $F_4$. It is found that 9 subjects show the best performance i.e. lowest Xie-Beni index for K=6 while only one shows better results with K=2. These are reported as $K_{min}$ in Table II. Also it is found that compared to using the $F_6$, only $F_2$ for subjects S3, S4, S8 and S10; or only $F_4$ for subjects S5, S6 and S7 gives better results. Thus feature $F_7$ is selected as it gives a better performance compared to $F_6$ for eight out of ten subjects.

Next the distance between cluster centroids for each ECTs is computed. Let, say that for K number of clusters, $^KC_2$ different combinations of distances between clusters are obtained. From the given number of combinations, the cluster centers having minimum and maximum distance for each individual are identified. A study on these distance pairs with respect to relation with Bloom's categories is presented in Table III. Here the attempt is to group subjects with similar relative cognitive skills. As for example, it can be seen from the Table III that it can be inferred for S1, S2 and S3 the FN-HP pair is having minimum distance i.e. maximum similarity. Here, S7 is neglected as number of clusters with minimum Xie-Beni index is 2 which is different from all the remaining subjects.

TABLE III

Cluster centers with minimum and maximum distances

| Subjects | Pair with min/max distance between centroids | Remarks |
|---|---|---|
| S1 | Min: FN-HP<br>Max: SX-VP | Min: Though they are from separate categories, the subject treats number as a pattern.<br>Max: Though both are in same category, the alphabets and shapes are treated differently. |
| S2 | Min: FN-HP<br>Max: FN-GC | Min: Though they are from separate categories, the subject treats number as a pattern.<br>Max: Same categories but FN needs remembering also. |
| S3 | Min: FN-HP<br>Max: FN-GC | Min: Though are from separate categories, the subject treats number as a pattern.<br>Max: Same categories but FN needs remembering also |
| S4 | Min: FA-SX<br>Max: FN-GC | Min: Different category but, searching "A" (in FA) is similar to searching "X" (in SX).<br>Max: Same categories but FN needs remembering also |
| S5 | Min: GC-VP<br>Max: FN-VP | Min: They are from same category and are treated similarly as both are related to patterns.<br>Max: Same category but the numbers and patterns are treated differently. |
| S6 | Min: GC-VP<br>Max: GC-HP | Min: They are from same category and are treated similarly as both are related to patterns.<br>Max: Separate categories. |
| S8 | Min: FN-VP<br>Max: GC-HP | Min: Same category - numbers and patterns are treated similarly.<br>Max: Separate categories. |
| S9 | Min: FN-SX<br>Max: FN-HP | Min: Same category - numbers and patterns are treated similarly.<br>Max: Separate categories. |
| S10 | Min: SX-VP<br>Max: SX-GC | Min: Same category - the "X" (in SX) is treated as a pattern as in VP.<br>Max: Same category but for SX, user needs to remember as well. |

Following the unsupervised cluster analysis on the EEG features for segregating the cognitive categories, one or more metrics are introduced for EEG based identification of the Traits of Cognitive Perception (TCP) among different individuals. In one aspect of the disclosure, if $C_i$ and $C_j$ be the centers of the $i^{th}$ and the $j^{th}$ clusters respectively for a particular subject, the separation Index $(SI_{i,j})$ between these two clusters is given as (3), where $\|.\|$ denotes the Euclidean Distance between them.

$$SI_{i,j} = \|C_i - C_j\| \quad (3)$$

If, say there are N number of clusters formed, $^NC_2$ pair-wise $SI_{i,j}$ values are obtained. Next, search is made for the pair of clusters that lead to the maximum and minimum separation index values $SI_{min}$ and $SI_{max}$ for each subject. Further, the ratio $S_r$ of $SI_{min}$ upon $SI_{max}$ is computed as can be seen in equations. (4), (5) and (6) below.

$$SI_{min} = \text{minimum}(S_{i,j}) \quad (4)$$

$$SI_{max} = \text{maximum}(S_{i,j}) \quad (5)$$

$$S_r = SI_{min}/SI_{max} \quad (6)$$

The above obtained $SI_{min}$, $SI_{max}$ and $S_r$ values are used as metrics to identify the TCP of a particular subject. While, it is obvious that $SI_{min}$ (or $SI_{max}$) determines the how similarly (or dissimilarly) a subject treats the pair of tasks, $S_r$ determines the spread of cognitive perception. A value of $S_r$ close to 1 indicates almost similar interpretation of all tasks by the subject. This pertains to the subject wise study of TCPs. Now, depending on the $SI_{min}$, $SI_{max}$ and $S_r$ values across all subjects, they are grouped into different categories of TCPs. This amounts to the stimulus-wise study of TCPs across all subjects.

Likewise, a similar approach can be used to analyze a new task (say $T_{new}$). In such a scenario a set of subjects are considered who belong to the same group of TCP. Then the EEG signal is captured by presenting the new task. The EEG signals are analyzed to understand the relative structure with respect to the $C_i$. Assuming that there are N ECTs, then $1 \leq i \leq N$. The centroid of the EEG features for the $T_{new}$ is $C_{new}$. Then the weight of each ECT present in the new task is given by equation (7) as follows.

$$W_i = 1 - \frac{C_i - C_{new}}{\sum_{i=1}^{N}(C_i - C_{new})} \quad (7)$$

In the interest of clarity, not all of the routine features of the implementations of the perceptual-cognitive-system and method are shown and described. It will, of course, be appreciated that in the development of any such actual implementation of the perceptual-cognitive system and method, numerous implementation-specific decisions may need to be made in order to achieve the system specific goals, and that these specific goals will vary from one implementation to another and from one application area to another.

It is to be understood that the invention is not limited in its application to the details of construction and parts illustrated in the accompanying drawings and described hereinabove. The invention is capable of other embodiments and of being practiced in various ways. It is also to be understood that the phraseology or terminology used herein is for the purpose of description and not limitation. Hence, although the present invention has been described hereinabove by way of illustrative embodiments thereof, it can be modified at will, within the scope of the appended claims, without departing from the spirit, scope and nature of the subject invention.

The invention claimed is:

1. A method for estimating or improvising perceptual-cognitive traits of a subject, the method being implemented by at least one processor and comprising:
   retrieving and pre-processing data and associated metadata indicative of brainwave activity of the subject to obtain effect of a plurality of elementary cognitive tasks, wherein the data comprises electroencephalogram (EEG) signals, and wherein processed EEG signals are analyzed by:
      partitioning the processed EEG signals into plurality of baseline and trial epochs;
      analyzing the baseline and trial epochs in a time frequency domain using an S-transform, and
      computing mean frequencies of the baseline and trial epochs to derive peak and average power shifts and corresponding frequency shifts thereof, and
      concatenating the peak powers and peak frequency shifts or average powers and average frequency shifts or a combination thereof to determine characterizing feature vectors between the baseline and trial epochs obtained from different frequency bands;
   identifying cognitive categories within a cognitive domain of a cognitive learning model;
   mapping a plurality of elementary cognitive tasks to be performed by the subject with identified cognitive categories;
   performing cluster analysis on each of the mapped elementary cognitive tasks and determining separation index values using the cluster analysis in relation to the identified cognitive categories; and
   generating metrics from the separation index values for estimation or improvisation of perceptual-cognitive traits of the subject.

2. The method of claim 1, wherein the elementary cognitive tasks are representative of one or more stimuli directly linked with cognitive perception of the subject.

3. The method of claim 1, wherein the electroencephalogram (EEG) signals captured using low resolution EEG devices and the associated metadata include time stamps for EEG signals, presentation time of a stimulus, instructions and baseline windows; time stamps and the entries of the subject responses.

4. The method of claim 3, further comprising, for each new elementary cognitive task to be performed by the subject:
   iteratively analyzing the EEG signals in response to the stimulus presented and receiving results representative therefrom; and
   deriving the separation index values with respect to previously formed clusters; and accordingly categorizing the subject based on perceptual-cognitive traits into a corresponding cluster.

5. The method of claim 1, wherein the cognitive learning model is Bloom's taxonomy.

6. The method of claim 5, wherein the Bloom's taxonomy comprises analyze, remember, apply, evaluate, create and understand.

7. The method of claim 1, wherein the pre-processing of the EEG signals further comprises:
   removing a voltage offset from received EEG signals;
   normalizing the EEG signals to zero mean;
   filtering to restrict the normalized signals within a predefined frequency range; and
   removing ocular artifacts using a Hilbert Huang Transform technique.

8. The method of claim 1, wherein the frequency bands are selected from alpha and theta frequency bands and a maximal information coefficient is used to determine if the peak powers and peak frequency shifts or average powers and average frequency shifts or a combination thereof is selected for determining the feature vectors.

9. The method of claim 1, wherein the cluster analysis is performed on the feature vectors of the EEG signals obtained from different frequency bands using a K-means model, and an optimum number of clusters to be formed is derived from a Xie-Beni index.

10. The method of claim 1, wherein the separation index between various clusters for each elementary cognitive task is based on a standardized Euclidean distance there between and determining the separation index values includes determining maximum and minimum values of the separation index between various clusters for each of the elementary cognitive tasks and a ratio of the minimum values against the maximum values to finally generate the metrics for cognitive traits.

11. A system for estimating and improvising perceptual-cognitive traits of a subject, comprising:
   a processor;
   a data bus coupled to the processor; and
   a computer-usable medium embodying computer code, said computer-usable medium being coupled to the data bus, the computer code comprising instructions executable by the processor and configured to cause the processor to perform a method comprising:
      retrieving and pre-processing data and associated metadata indicative of brainwave activity of the subject to obtain a plurality of elementary cognitive tasks, wherein the data comprises electroencephalogram (EEG) signals, and wherein processed EEG signals are analyzed by:
         partitioning the processed EEG signals into plurality of baseline and trial epochs;
         analyzing the baseline and trial epochs in a time frequency domain using an S-transform, and
         computing mean frequencies of the baseline and trial epochs to derive peak and average power shifts and corresponding frequency shifts thereof, and
         concatenating the peak powers and peak frequency shifts or average powers and average frequency shifts or a combination thereof to determine characterizing feature vectors between the baseline and trial epochs obtained from different frequency bands;
      identifying cognitive categories within a cognitive domain of a cognitive learning model;
      mapping a plurality of elementary cognitive tasks to be performed by the subject with identified cognitive categories;
      performing cluster analysis on each of the mapped elementary cognitive tasks and determining separation index values using the cluster analysis in relation to the identified cognitive categories; and
      generating metrics from the separation index values for estimation or improvisation of perceptual-cognitive traits of the subject.

12. The system of claim 11, wherein the pre-processing of the EEG signals further comprises:

removing a voltage offset from received EEG signals;

normalizing the EEG signals to zero mean;

filtering to restrict the normalized signals within a predefined frequency range; and removing ocular artifacts using a Hilbert Huang Transform technique.

13. The system of claim 11, wherein the electroencephalogram (EEG) signals and the associated metadata include time stamps for EEG signals, presentation time of a stimulus, instructions and baseline windows; time stamps and entries of subject responses.

14. The system of claim 13, wherein the processor, for each new elementary cognitive task to be performed by the subject, further:

iteratively analyzes the EEG signals in response to the stimulus presented and receives results representative therefrom; and derives the separation index values with respect to previously formed clusters; and accordingly categorizes the subject based on perceptual-cognitive traits into a corresponding cluster.

15. The system of claim 11, wherein the cognitive learning model is Bloom's taxonomy and the Bloom's taxonomy comprises analyze, remember, apply, evaluate, create and understand.

16. The system of claim 11, wherein a maximal information coefficient is used to determine if the peak powers and peak frequency shifts or average powers and average frequency shifts or a combination thereof is selected for determining the feature vectors.

17. The system of claim 11, wherein the cluster analysis is performed on the feature vectors of EEG signals obtained from different frequency bands using a K-means model, and an optimum number of clusters to be formed is derived from a Xie-Beni index.

18. The system of claim 11, wherein the separation index between various clusters for each elementary cognitive task is based on a standardized Euclidean distance there between and determining the separation index values includes determining maximum and minimum values of the separation index between various clusters for each of the elementary cognitive tasks and a ratio of the minimum values against the maximum values to finally generate the metrics.

* * * * *